(12) United States Patent
Negrisoli et al.

(10) Patent No.: US 8,765,798 B2
(45) Date of Patent: Jul. 1, 2014

(54) PEPTIDE DERIVATIVES WITH THERAPEUTIC ACTIVITY

(75) Inventors: Gianpaolo Negrisoli, Bergamo (IT); Renato Canevotti, Chignolo d'Isola (IT)

(73) Assignee: Flamma S.p.A., Chignolo d'Isola (IT)

( * ) Notice: Subject to any disclaimer, the term of this patent is extended or adjusted under 35 U.S.C. 154(b) by 340 days.

(21) Appl. No.: 12/306,259

(22) PCT Filed: Jun. 15, 2007

(86) PCT No.: PCT/IB2007/001602
§ 371 (c)(1),
(2), (4) Date: Apr. 23, 2009

(87) PCT Pub. No.: WO2008/001174
PCT Pub. Date: Jan. 3, 2008

(65) Prior Publication Data
US 2009/0247601 A1    Oct. 1, 2009

(30) Foreign Application Priority Data
Jun. 23, 2006 (IT) .............. MI2006A1218

(51) Int. Cl.
*A61K 31/4172* (2006.01)
*C07D 233/64* (2006.01)

(52) U.S. Cl.
CPC .......... *A61K 31/4172* (2013.01); *C07D 233/64* (2013.01)
USPC ...................... 514/400; 548/339.1

(58) Field of Classification Search
CPC .......... C07D 233/64; A61K 31/4172
USPC .............. 548/338.1, 339.1; 514/399, 400
See application file for complete search history.

(56) References Cited

FOREIGN PATENT DOCUMENTS

| EP | 0500332 A2 | 8/1992 |
| EP | 1297830 A1 | 4/2003 |
| WO | WO 2005120543 A1 * | 12/2005 |

OTHER PUBLICATIONS

Cacciatore et al., "Biochemical Properties of New Synthetic Carnosine Analogues Containing the Residue of 2,3,-diaminopropionic acid: the Effect of N-acetylation", Amino Acids 28:77-83 (2005).*

Babizhayev, Mark A., "Biological Activities of the Natural Imidazole-Containing Peptidomimetics n-acetylcarnosine, carcinine and L-carnosine in Ophthalmic and Skin Care Products", Life Sciences, Pergamon Press, Oxford, GB, 78(20):2343-2357 (2006).

Orioli et al., "LC-ESI-MS/MS Determination of 4-hydroxy-trans-2-nonenal Michael Adducts with Cysteine and Histidine-containing Peptides as Early Markers of Oxidative Stress in Excitable Tissues," J Chemo B: Biomed Sci Appl 827(1):109-118 (2005).

* cited by examiner

*Primary Examiner* — Joseph Kosack
*Assistant Examiner* — Matthew Coughlin
(74) *Attorney, Agent, or Firm* — Porzio, Bromberg & Newman, P.C.

(57) ABSTRACT

Dipeptide compounds containing a histidine residue proved to have interesting blocking activity on secondary products from lipid oxidative stress, in particular on unsaturated aldehydes such as malondialdehyde and hydroxynonenal, which are known to contribute to the inset of quite a number of chronic pathologies such as neurodegenerative, inflammatory chronic, cardiovascular diseases, diabetes complications and cataract.

3 Claims, No Drawings

PEPTIDE DERIVATIVES WITH THERAPEUTIC ACTIVITY

CROSS REFERENCE TO RELATED APPLICATION

This is a National Stage of International Application PCT/IB2007/001602, filed 15 Jun. 2007, the disclosure of which is incorporated by reference herein and which claims the benefit of Application No. MI2006A001218, filed in Italy on 23 Jun. 2006.

The present invention relates to histidine peptide derivatives, and compositions containing them.

PRIOR ART

It has been extensively demonstrated that oxidative damage is involved in the aetiogenesis and/or progress of various physio-pathological processes, including aging, inflammatory disorders, diabetes, cardiovascular disease and neurodegenerative processes. Among the main molecular mechanisms responsible for oxidative damage, a crucial role is played by structural damage to proteins, lipids and nucleic acids induced by free-radical reactive oxygen species, and by an altered cell redox state [Halliwell B, Gutteridge J M. Free Radicals in Biology and Medicine (2001) Oxford Science Publications, 3rd Ed.].

It has also been suggested that some products of lipid oxidation characterised by a keto/aldehyde function act as important cytotoxic oxidative mediators, causing irreversible structural modifications of the biomolecules, with consequent alteration of cell functionality [Esterbauer H. et al., Free Radic. Biol. Med. 1991; 11:81-128; Uchida K. Free Radic. Biol. Med. 2000; 28:1685-96; Poli G. et al., IUBMB Life. 2000; 50:315-21].

Among the carbonyl compounds studied, the products of oxidation of polyunsaturated fatty acids, including alpha, beta-unsaturated aldehydes such as 4-hydroxy-trans-2-nonenal (HNE) and acrolein (ACR), are of considerable scientific interest. The high biological response of these derivatives is attributable to their electrophilic nature, which entails an addition/conjugation reaction with the nucleophilic sites present in the proteins (histidine, lysine and cysteine residues) and nucleic acids (deoxyguanosine), with a consequent alteration of the cell response/function and a potential mutagenic effect [Esterbauer H. et al., Free Radic. Biol. Med. 1991; 11:81-128].

The involvement of unsaturated aldehydes in various pathological processes with an oxidative basis has been demonstrated with the use of mono- and polyclonal antibodies [Uchida K. 4-Hydroxy-2-nonenal: a product and mediator of oxidative stress. Prog. Lipid Res. 2003; 42:318-43]. In particular, adducts between HNE and acrolein with proteins have been identified in biopsy and autopsy tissue of patients suffering from diabetes, atherosclerosis, muscular dystrophy, rheumatoid arthritis, actinic elastosis, cerebral ischaemia and neurodegenerative diseases such as Alzheimer's disease and Parkinson's disease [Uchida K. Prog. Lipid Res. 2003; 42:318-43; Zarkovic N. Mol. Aspects Med. 2003; 24:281-91; Zarkovic N. Mol. Aspects Med. 2003; 24:293-303; M. Carini et al. in "Redox Proteomics: from Protein Modifications to Cellular Dysfunction and Diseases" (Ed. I. Dalle-Donne, A. Scaloni, and A. Butterfield); Wiley InterScience Books from John Wiley & Sons (2005).]

The role of HNE as a pathogenetic factor has been demonstrated at molecular level for various disorders, including fibrosis [Chiarpotto E. et al., Biofactors. 2005; 24(1-4):229-36], diabetic nephropathy [Furfaro A L. et al. Biofactors. 2005; 24(1-4):291-8], atherosclerotic processes [Leonarduzzi G. et al., Mol Nutr Food Res. 2005 November; 49(11): 1044-9], and neurodegenerative disorders [Zarkovic K. Mol Aspects Med. 2003 August-October; 24(4-5):293-303].

It is therefore evident that carbonyl processes, especially reactive carbonyl compounds such as HNE, are important targets for the development of a new class of biologically active molecules with carbonyl-quenching activity.

DISCLOSURE OF THE INVENTION

The present invention relates to dipeptide compounds containing a histidine residue which proved to have interesting blocking activity on secondary products from lipid oxidative stress, in particular on unsaturated aldehydes such as malondialdehyde and hydroxynonenal, which are known to contribute to the onset of quite a number of chronic pathologies such as neurodegenerative, inflammatory chronic, cardiovascular diseases, diabetes complications and cataract.

The invention further relates to the use of said compounds for the treatment or the prevention of said pathologies.

The compounds of the invention have the general formula I

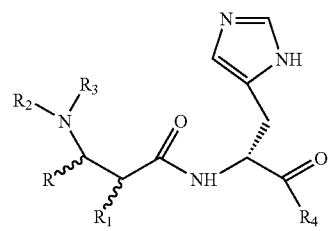

in which:

R and $R_1$ which can be the same or different, are:

- hydrogen, with the proviso that at least one of them is not hydrogen;
- a straight or branched $C_1$-$C_8$ or cyclic $C_3$-$C_7$ alkyl group;
- an aryl-$C_1$-$C_5$-alkyl or heteroaryl-$C_1$-$C_5$-alkyl group;
- an aryl or heteroaryl group;
- a free amino group, except when $R_1$ is an amino group and R, $R_2$, $R_3$ and $R_4$ are hydrogen, or an amino group optionally substituted with an alkylcarbonyl, arylcarbonyl, heteroarylcarbonyl, arylalkylcarbonyl, heteroarylalkylcarbonyl, alkyloxycarbonyl, or arylalkyloxycarbonyl group;
- a hydrazine, hydroxylamino or guanidine group;
- a hydroxy group optionally substituted with a $C_1$-$C_5$ alkyl, aryl or arylalkyl group;

or:

R and $R_1$, taken together, form compounds of formula II in which X and Y, which can be the same or different, are a sulfur, nitrogen, or oxygen atom or a $CH_2$ group, n and m, which can be the same or different, have a value ranging from 0 to 5;

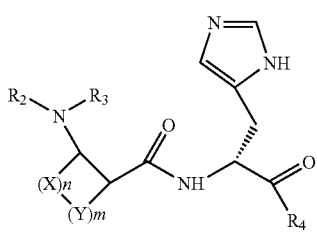

or
R and $R_1$, taken together, form a double bond to give compounds of formula III;

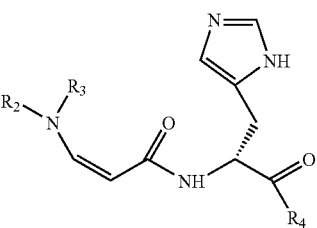

$R_2$ and $R_3$, which can be the same or different, are:
   hydrogen,
   a straight or branched $C_1$-$C_{20}$ or cyclic $C_3$-$C_7$ alkylcarbonyl group optionally containing one or more double bonds, an arylcarbonyl or arylalkylcarbonyl group,
   a straight or branched $C_1$-$C_{10}$ or cyclic $C_3$-$C_7$ alkyloxycarbonyl group optionally containing one or more double bonds, an aryloxycarbonyl or arylalkyloxycarbonyl group,
   an amino group,
   a hydroxy group,
   a group of general formula IV

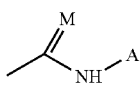

in which M is nitrogen, oxygen or sulfur and A is hydrogen or an amino group;
$R_4$ is:
   a hydroxy group,
   an amino group optionally mono or disubstituted by groups, which can be the same or different, selected from:
      a straight or branched $C_1$-$C_{20}$ or cyclic $C_3$-$C_7$ alkyl group, optionally containing one or more double bonds,
      an aryl or arylalkyl group,
      a straight or branched $C_1$-$C_{20}$ or cyclic $C_3$-$C_7$ alkyloxycarbonyl group, optionally containing one or more double bonds,
      an aryl, heteroaryl, heteroarylalkyl or arylalkyl group,
      a straight or branched $C_1$-$C_{10}$ or cyclic $C_3$-$C_7$ alkoxy group, optionally containing one or more double bonds,
      an alkoxycarbonyloxyalkoxy or alkylcarbonyloxyalkoxy group bearing a straight, branched or cyclic alkyl,
      an aryloxy, heteroaryloxy, heteroarylalkyloxy or arylalkoxy group.

The invention also comprises any diastereomers of the compounds of general formula I, II or III, singularly i.e. in a mixture thereof in any ratio, the pharmaceutically acceptable salts thereof as well as the complexes of the compounds with metal cations such as zinc or copper.

The aryl or heteroaryl moieties of the aryl, heteroaryl, aryl-alkyl, heteroaryl-alkyl, arylcarbonyl, heteroarylcarbonyl, heteroarylalkylcarbonyl, arylalkylcarbonyl, aryloxycarbonyl, arylalkyloxycarbonyl, aryloxy, heteroaryloxy, heteroarylalkyloxy, arylalkoxy, arylsulfonyl groups defined above can be mono- or polycyclic and optionally substituted with one or more substituents selected from:
   hydroxy, methoxy, $C_1$-$C_5$-alkoxycarbonyl groups;
   amino, $C_1$-$C_5$-mono- or di-alkylamino, $C_1$-$C_5$-acylamino groups;
   halogen atoms such as Cl, Br, F, I;
   straight or branched or cyclic alkyl groups.
Preferred alkyl, alkyloxycarbonyl, alkoxy or alkoxycarbonyl groups are those in which the alkyl group is methyl, ethyl, propyl, isopropyl, n-butyl, sec-butyl, tert-butyl, n-pentyl, n-hexyl, n-octyl, n-decyl.
Preferred cycloalkyl groups are cyclopropyl, cyclopentyl and cyclohexyl.
By "aryl group or residue" preferably phenyl or naphthyl is meant, more preferably phenyl, optionally substituted with hydroxy, methyl, cyclopropyl, methoxy, amino, dimethylamino, methylamino, ethylamino, diethylamino, acetylamino, formylamino, propionylamino, butanoylamino groups, halogen atoms.
A preferred aralkyl group is benzyl or phenethyl.
By "hetaryl group or residue" preferably imidazolyl, pyridyl, pyrimidinyl, pyrazinyl, thienyl, furoyl, thiazolyl, triazolyl, oxazolyl are meant.
Preferred compounds of formula I are those in which:
a) $R_1$ is hydrogen, R is an alkyl, aryl or aralkyl group as defined above;
b) $R_1$ is an amino group and R is hydrogen;
c) $R_1$ is an alkyl, aryl or aralkyl group as defined above and R is hydrogen;
d) $R_2$ and $R_3$ are hydrogen, alkylcarbonyl, alkoxycarbonyl arylcarbonyl or arylalkoxycarbonyl whereas R and $R_1$ have the preferred meanings as indicated at items a)-c);
e) $R_4$ is alkoxy whereas R, $R_1$, $R_2$ and $R_3$ have the preferred meanings as indicated at items a-d.

The compounds of the invention were prepared using some of the well-known solid phase or solution procedures for the peptide synthesis as reported in literature for example in Houben-Weil "Synthesis of peptides and peptidomimetics" vol. E22 a-d or in J. Jones "Amino acid and peptide synthesis". The amino acids used in the synthesis, when not available in the already protected form, were suitably functionalized with the necessary protective groups using established procedures, such as those reported in T. W. Greene, P. G. M. Wuts "Protective group in organic synthesis" or in P. J. Kocienski "Protecting groups".

The resulting final products, when necessary, were purified according to any procedures well known to those skilled in the art using, for example crystallizations, chromatographic purifications or any other technique necessary to obtain the compounds in the required purity degree.

The pharmacological activity of the compounds of the invention was determined in vitro evaluating their carbonyl-quenching activity on 4-hydroxy nonenal (HNE), which is known to be involved in a number of pathologies.

For the intended uses, the compounds of formula I, II or III are conveniently formulated in conventional pharmaceutical, cosmetic or nutritional compositions, suitable for the administration through the oral, parenteral, topical or transdermal route. Said compositions are a further object of the invention. Examples of said compositions are capsules, tablets, syrups, injectable solutions or suspensions, ointments, suppositories, controlled-release forms and the like, water-soluble granulates. Said forms, in addition to the carriers and excipients used in the pharmaceutical technique, may optionally contain other active ingredients having complementary or anyway useful activity for the treatment/prevention of the concerned pathologies.

The invention is illustrated in detail by the following examples.

General Method for the Synthesis of the Dipeptide Derivatives 1.2 eq of Fmoc-D-Hys(Trt)-OH are coupled to a Chlorotrityl PS resin in dimethylformamide (DMF) in the presence of 3 eq of diisopropylethylamine. The Fmoc group is removed by two treatments with a piperidine/DMF 25/75 solution for 15 minutes. A solution of 2 eq of the suitable Boc-amino acid, 2 eq of PyBop and 2 eq of HOBT in DMF is then added in the reactor containing the resin, followed by 5 eq of diisopropylethylamine. The completion of the reaction is monitored by Kaiser test. After suitable washing, the peptide is cleaved from resin using a trifluoroacetic acid solution containing 5% water in dichloromethane. The crude peptide is recovered from the solution by precipitation using a suitable solvent, usually an ether. The crude peptide is then purified by preparative HPLC using reverse-phase columns and eluting with water and acetonitrile mixtures. The fractions containing the pure product are concentrated to remove acetonitrile and then freeze-dried to obtain the solid product.

Following this procedure, the following exemplary compounds were prepared:

(3S)-3-amino-3-phenylpropanoyl-D-histidine (FL-926-A-006)

$^1$H-NMR (DMSO-D6): 8.47-8.45 (1H, d), 7.69 (1H, s), 7.55-7.41 (5H, m), 6.88 (1H, s), 4.69-4.65 (1H, t), 4.38-4.34 (1H, m), 3.15-3.08 (1H, dd), 2.90-2.73 (3H, m). $^{13}$C-NMR (DMSO-D6): 172.54, 168.80, 138.27, 135.01, 134.08, 129.16, 128.96, 127.48, 117.13, 54.05, 52.22, 41.12, 29.30.

(3S)-3-aminobutanoyl-D-histidine (FL-926-A-002)

$^1$H-NMR (D$_2$O): 8.38 (1H, s), 7.20 (1H, s), 4.51-4.46 (1H, dd), 3.71-3.65 (1H, m), 3.27-3.20 (1H, dd), 3.11-3.03 (1H, dd), 2.72-2.53 (2H, m), 1.28-1.26 (3H, d).

$^{13}$C-NMR (D$_2$O): 176.65, 171.19, 133.67, 130.37, 116.83, 54.23, 44.87, 38.97, 27.47, 23.19.

(2R,3S)-3-amino-2-hydroxy-4-phenylbutanoyl-D-histidine (FL-926-A-005)

$^1$H-NMR (DMSO-D6): 8.20-8.18 (1H, d), 7.65 (1H, s), 7.40-7.28 (5H, m), 6.89 (1H, s), 4.38-4.32 (1H, s), 4.20-419 (1H, d), 3.59 (1H, bs), 3.13-2.80 (4H, m).

$^{13}$C-NMR (DMSO-D6): 172.53, 170.88, 137.50, 135.14, 134.18, 129.93, 128.89, 127.05, 117.35, 71.19, 56.30, 54.04, 34.32, 28.95.

Pharmacological Assays

The carbonyl-quenching activity of a selected series of compounds of the present invention was assessed in vitro, incubating HNE (50 μM) with the tested compounds (1 mM), in phosphate buffer (10 mM) pH 7.4 at 37° C. The activity was evaluated after one, two and three hours incubation, determining the residual content of HNE by reversed-phase chromatography as described by Aldini G et al. [Biochem Biophys Res Commun. 2002 Nov. 15; 298(5):699-706]. The carbonyl-quenching activity is expressed as the reacted HNE percent compared with the HNE content in the absence of the test compounds.

The results summarized in Table I evidence that all of the tested compounds are active, although to different extents. Carnosine was used as the reference, in view of its well known carbonyl-quenching activity, in particular on alpha,beta unsaturated aldehydes such as HNE [Aldini G et al.: Biofactors. 2005; 24(1-4):77-87; Aldini G. et al.: Biochem Biophys Res Commun. 2002 Nov. 15; 298(5):699-706]. Surprisingly, a series of compounds of the invention proved significantly more active than carnosine and in the case of compound FL-926-A-006 such activity was almost twice as high, after one hour incubation.

| Peptide | reacted HNE (%) t = 1 h | | | reacted HNE (%) t = 2 h | | | reacted HNE (%) t = 3 h | | |
| --- | --- | --- | --- | --- | --- | --- | --- | --- | --- |
| | mean | sd | n | mean | sd | n | mean | sd | n |
| Carnosine | 17.39258 | 2.624364 | 3 | 31.64978 | 5.327186 | 3 | 43.58841 | 5.389527 | 3 |
| FL-926-A-006 | 29.29545 | 1.713309 | 3 | 50.7209 | 2.821651 | 3 | 65.8531 | 3.323709 | 3 |
| FL-926-A-005 | 15.19785 | 1.726473 | 3 | 27.74705 | 2.454019 | 3 | 38.55761 | 3.423049 | 3 |
| FL-926-A-002 | 6.568469 | 0.8950699 | 3 | 14.26104 | 1.60434 | 3 | 21.58051 | 0.4358103 | 3 |

The invention claimed is:

1. Compounds of general formula I

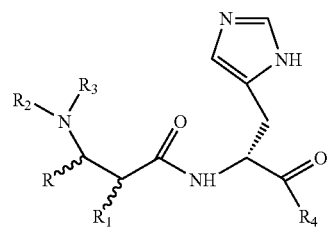

in which:
one of R and R$_1$ is hydrogen:
and the other is selected from
an aryl-C$_1$-C$_5$-alkyl, heteroaryl-C$_1$-C$_5$-alkyl group; or
an aryl or heteroaryl group optionally substituted with a group selected from hydroxy, methoxy, amino, C$_1$-C$_5$-mono- or di-alkylamino, C$_1$-C$_5$-acylamino groups, straight or branched or cyclic alkyl groups, and halogen atom;

$R_2$, $R_3$ and $R_4$ are hydrogen, or an amino group optionally substituted with an alkylcarbonyl, arylcarbonyl, heteroarylcarbonyl, arylalkylcarbonyl, heteroarylalkylcarbonyl, alkyloxycarbonyl, or arylalkyloxycarbonyl group;

or:

R and $R_1$, taken together, form compounds of formula II in which X and Y, which can be the same or different, are a sulfur, nitrogen, or oxygen atom or a $CH_2$ group, n and m, which can be the same or different, have a value ranging from 0 to 5;

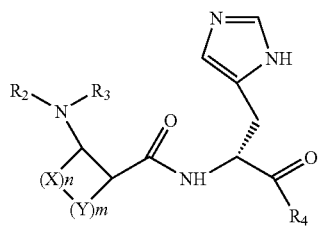

II or

R and $R_1$, taken together, form a double bond to give compounds of formula III;

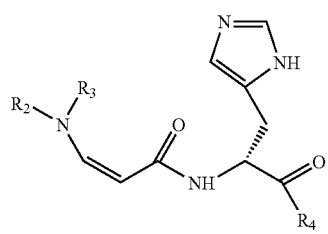

III $R_2$ and $R_3$, which can be the same or different, are:
hydrogen,
a straight or branched $C_1$-$C_{20}$ or cyclic $C_3$-$C_7$ alkylcarbonyl group optionally containing one or more double bonds, an arylcarbonyl or arylalkylcarbonyl group,
a straight or branched $C_1$-$C_{10}$ or cyclic $C_3$-$C_7$ alkyloxycarbonyl group optionally containing one or more double bonds, an aryloxycarbonyl or arylalkyloxycarbonyl group,
an amino group,
a hydroxy group,
a group of general formula IV

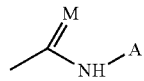

IV in which M is nitrogen, oxygen or sulfur and A is hydrogen or an amino group;

$R_4$ is:
a hydroxy group,
an amino group optionally mono or disubstituted by groups, which can be the same or different, selected from:
a straight or branched $C_1$-$C_{20}$ or cyclic $C_3$-$C_7$ alkyl group, optionally containing one or more double bonds,
an aryl or arylalkyl group, and
a straight or branched $C_1$-$C_{20}$ or cyclic $C_3$-$C_7$ alkyloxycarbonyl group, optionally containing one or more double bonds,
an aryl, heteroaryl, heteroarylalkyl or arylalkyl group,
a straight or branched $C_1$-$C_{10}$ or cyclic $C_3$-$C_7$ alkoxy group, optionally containing one or more double bonds,
an alkoxycarbonyloxyalkoxy or alkylcarbonyloxyalkoxy group bearing a straight, branched or cyclic alkyl,
an aryloxy, heteroaryloxy, heteroarylalkyloxy or arylalkoxy group.

2. A compound selected from
(3S)-3 amino-4-(4-hydroxyphenyl)butanoyl-D-histidine;
(3S)-3-amino-3-(4-methoxyphenyl)propanoyl-D-histidine;
(3S)-3-amino-3-phenylpropanoyl-D-histidine;
3-amino-2 phenylpropanoyl-D-histidine;
(3S)-3-amino-4-phenylbutanoyl-D-histidine;
(2R,3S)-3-amino-2-hydroxy-4-phenylbutanoyl-D-histidine; and
(3S)-3 amino-4-(4-methoxyphenyl)butanoyl-D-histidine.

3. A pharmaceutical composition containing an effective amount of a compound of claim 1 in combination with suitable excipients.

* * * * *